United States Patent
Munkelt

(10) Patent No.: US 9,059,524 B2
(45) Date of Patent: Jun. 16, 2015

(54) SOCKET ARRANGEMENT FOR AN ELECTROMEDICAL DEVICE

(71) Applicant: ERBE Elektromedizin GmbH, Tuebingen (DE)

(72) Inventor: Katja Munkelt, Hermsdorf (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 122 days.

(21) Appl. No.: 13/870,725

(22) Filed: Apr. 25, 2013

(65) Prior Publication Data

US 2013/0288500 A1   Oct. 31, 2013

(30) Foreign Application Priority Data

Apr. 26, 2012   (EP) ..................................... 12165760

(51) Int. Cl.
| | |
|---|---|
| H01R 13/64 | (2006.01) |
| H01R 13/00 | (2006.01) |
| H01R 13/15 | (2006.01) |
| A61B 18/12 | (2006.01) |

(Continued)

(52) U.S. Cl.
CPC ............ *H01R 13/15* (2013.01); *A61B 18/1233* (2013.01); *A61B 18/14* (2013.01); *A61B 2018/00178* (2013.01)

(58) Field of Classification Search
CPC ..................... H01R 24/58; A61B 2018/00178
USPC ............... 439/909, 668, 669, 246; 607/36, 37
See application file for complete search history.

(56) References Cited

U.S. PATENT DOCUMENTS

| | | |
|---|---|---|
| 5,621,256 A | 4/1997 | Crane et al. |
| 5,637,006 A * | 6/1997 | Almeras ....................... 439/587 |
| 6,074,386 A | 6/2000 | Goble et al. |

(Continued)

FOREIGN PATENT DOCUMENTS

| | | |
|---|---|---|
| CN | 1209047 A | 2/1999 |
| DE | 214724 A1 | 10/1984 |

(Continued)

OTHER PUBLICATIONS

European Search Report, related Application No. EP 12165760, Aug. 20, 2012, 6 pages.

(Continued)

*Primary Examiner* — Briggitte R Hammond
(74) *Attorney, Agent, or Firm* — Fitch, Even, Tabin & Flannery, LLP

(57) ABSTRACT

The invention relates to a socket arrangement (15) comprising at least one plug connector socket (18). Each plug connector socket (18) comprises a contact arrangement (28) with two electrically conductive contact elements (35, 36) and a spring arrangement (38). The two contact elements (35, 36) are supported so as to be movable relative to each other in a movement direction (B) at a right angle or obliquely with respect to a plug-in direction (R). The spring arrangement (38) acts on one or both contact elements (35, 36) in movement direction (B). Due to the pretensioning force of the spring arrangement (38), the two contact elements (35, 36) are pushed or pulled toward each another. With the plug contact pin (19) inserted in the plug connector socket (18), the two contact elements are moved toward each other in movement direction (B) and abut from different sides against the plug contact pin (19). As a result of this, a mechanical clamping effect and an electrical contact are provided.

18 Claims, 6 Drawing Sheets

Figure 1:
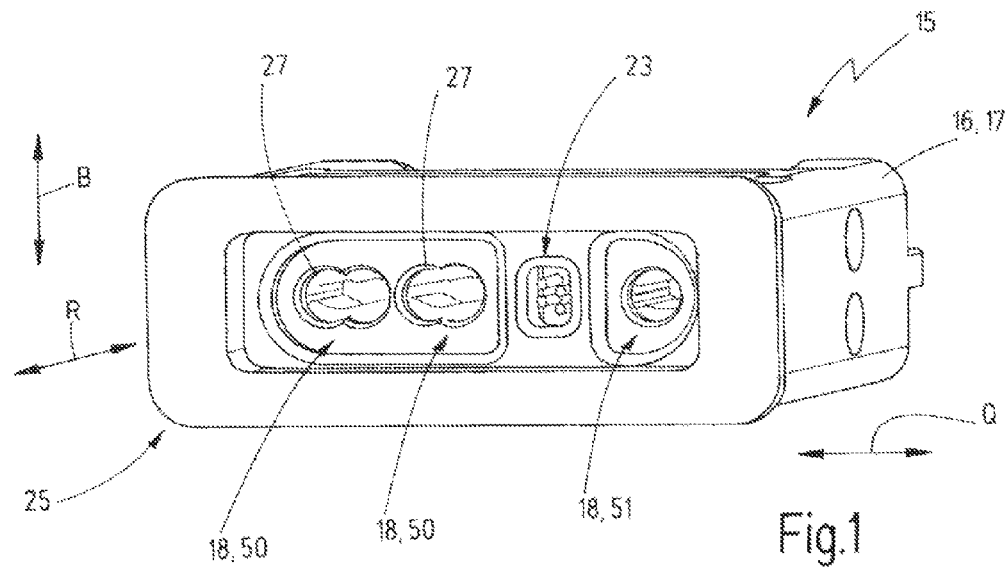

(51) Int. Cl.
*A61B 18/14* (2006.01)
*A61B 18/00* (2006.01)

(56) References Cited

U.S. PATENT DOCUMENTS

| | | | |
|---|---|---|---|
| 6,895,276 B2 * | 5/2005 | Kast et al. | 439/909 |
| 6,934,588 B1 * | 8/2005 | Brand et al. | 607/37 |
| 7,035,689 B1 | 4/2006 | Hawkins et al. | |
| 7,058,452 B2 * | 6/2006 | Dahlberg | 439/909 |
| 7,070,455 B2 * | 7/2006 | Balsells | 439/668 |
| 7,195,523 B2 * | 3/2007 | Naviaux | 439/827 |
| 7,255,615 B2 | 8/2007 | Woelfl et al. | |
| 8,131,370 B2 * | 3/2012 | Janzig et al. | 607/37 |
| 8,267,708 B1 * | 9/2012 | Sochor | 439/289 |
| 8,480,437 B2 * | 7/2013 | Dilmaghanian et al. | 439/669 |
| 2002/0128692 A1 | 9/2002 | Imani et al. | |
| 2004/0064164 A1 * | 4/2004 | Ries et al. | 607/37 |
| 2005/0027327 A1 | 2/2005 | Ries et al. | |
| 2011/0045680 A1 | 2/2011 | Beller et al. | |
| 2013/0252461 A1 * | 9/2013 | Gross | 439/577 |

FOREIGN PATENT DOCUMENTS

| | | |
|---|---|---|
| DE | 102007061483 A1 | 7/2009 |
| JP | S48-88484 | 10/1973 |
| JP | S52-044369 | 3/1977 |
| JP | S56-15576 U | 2/1981 |
| JP | H11-288766 A | 10/1999 |
| JP | 2001-244034 A | 9/2001 |
| JP | 2006-134878 A | 5/2006 |

OTHER PUBLICATIONS

Office Action in corresponding Japanese application No. 2013-089526 dated Jul. 29, 2014, 6 pages.
Office Action in corresponding Chinese application No. 201310147622.2 dated Dec. 24, 2014, 24 pages.

* cited by examiner

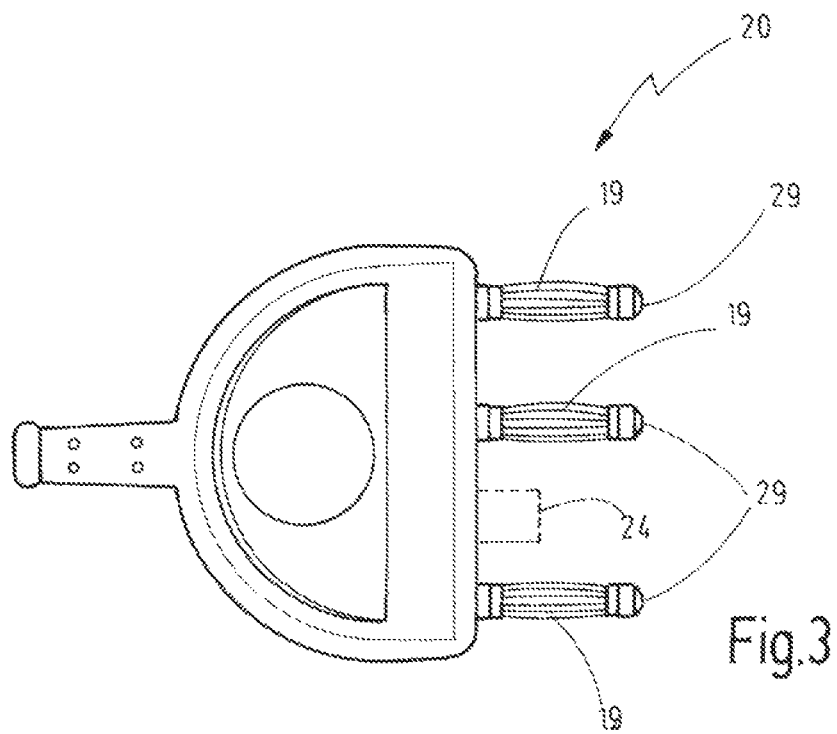
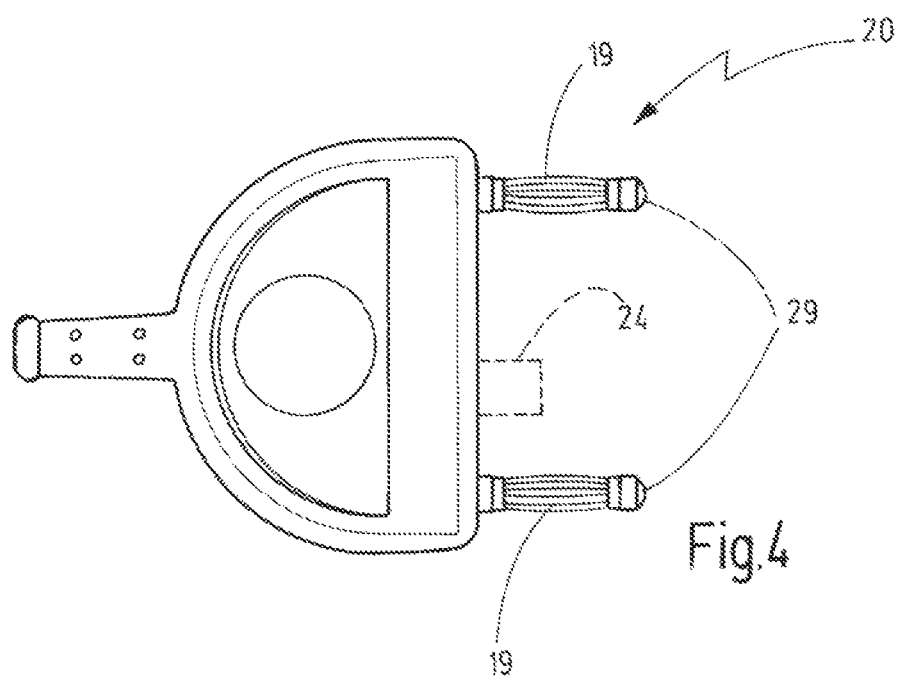

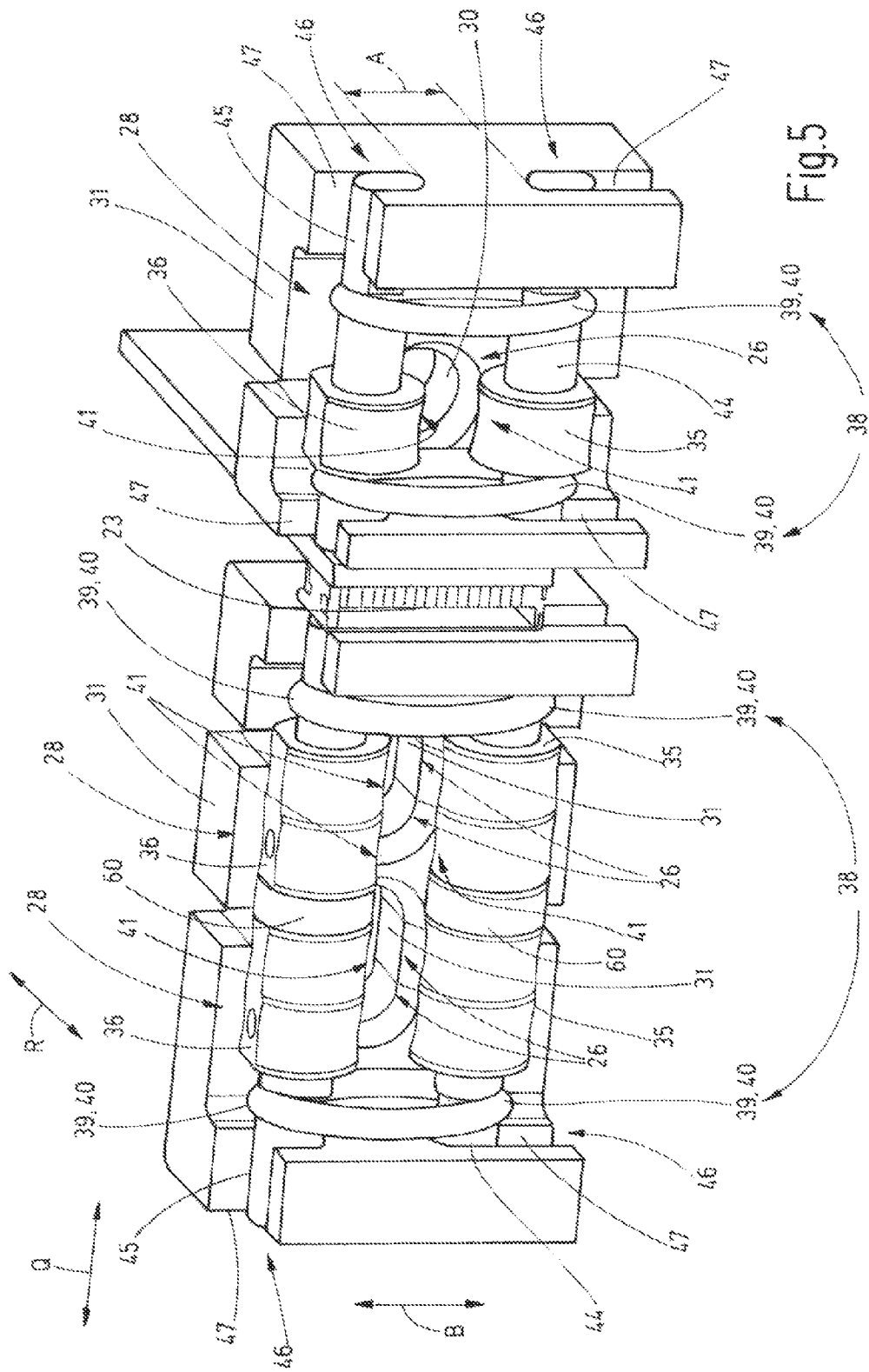

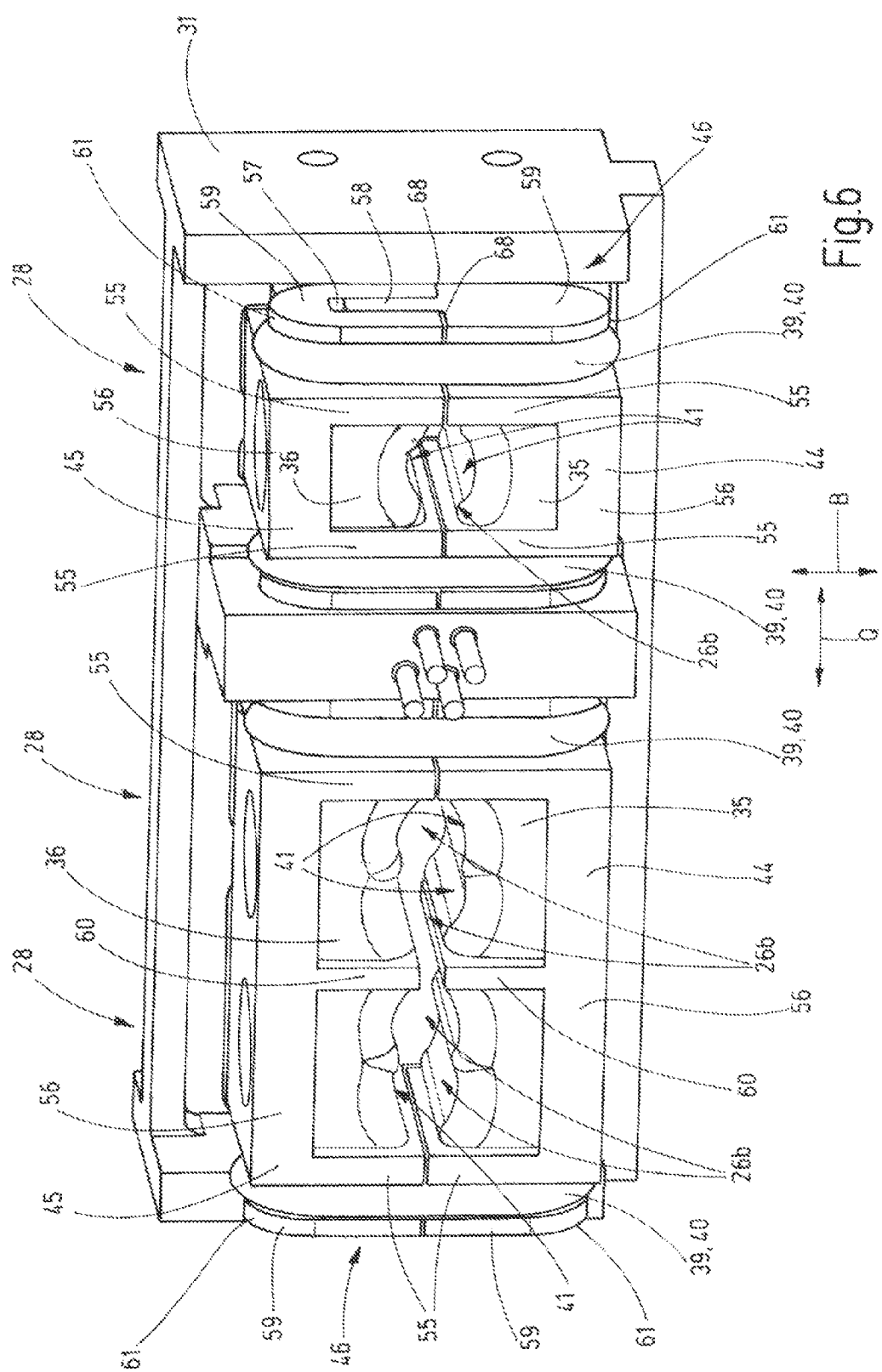

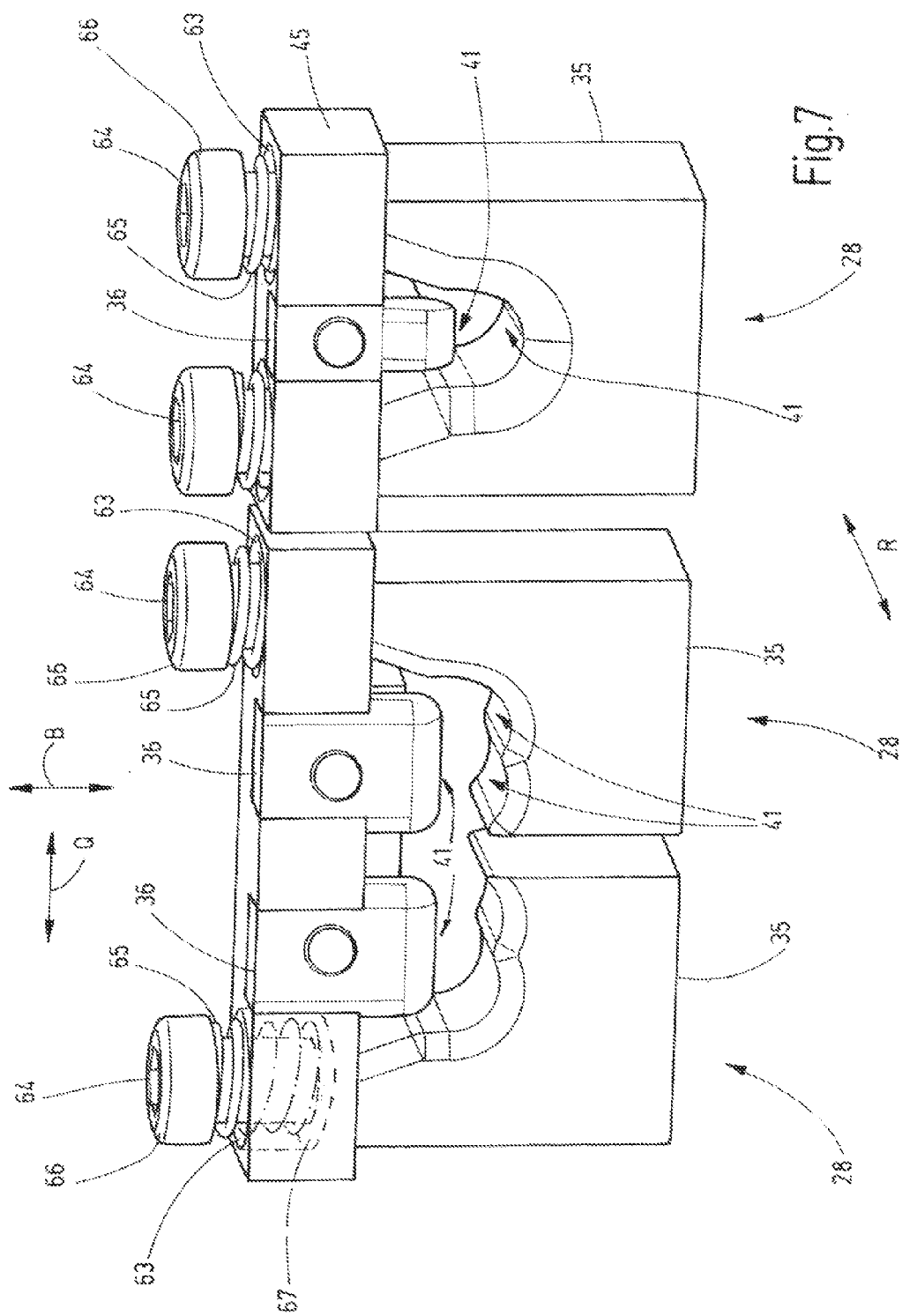

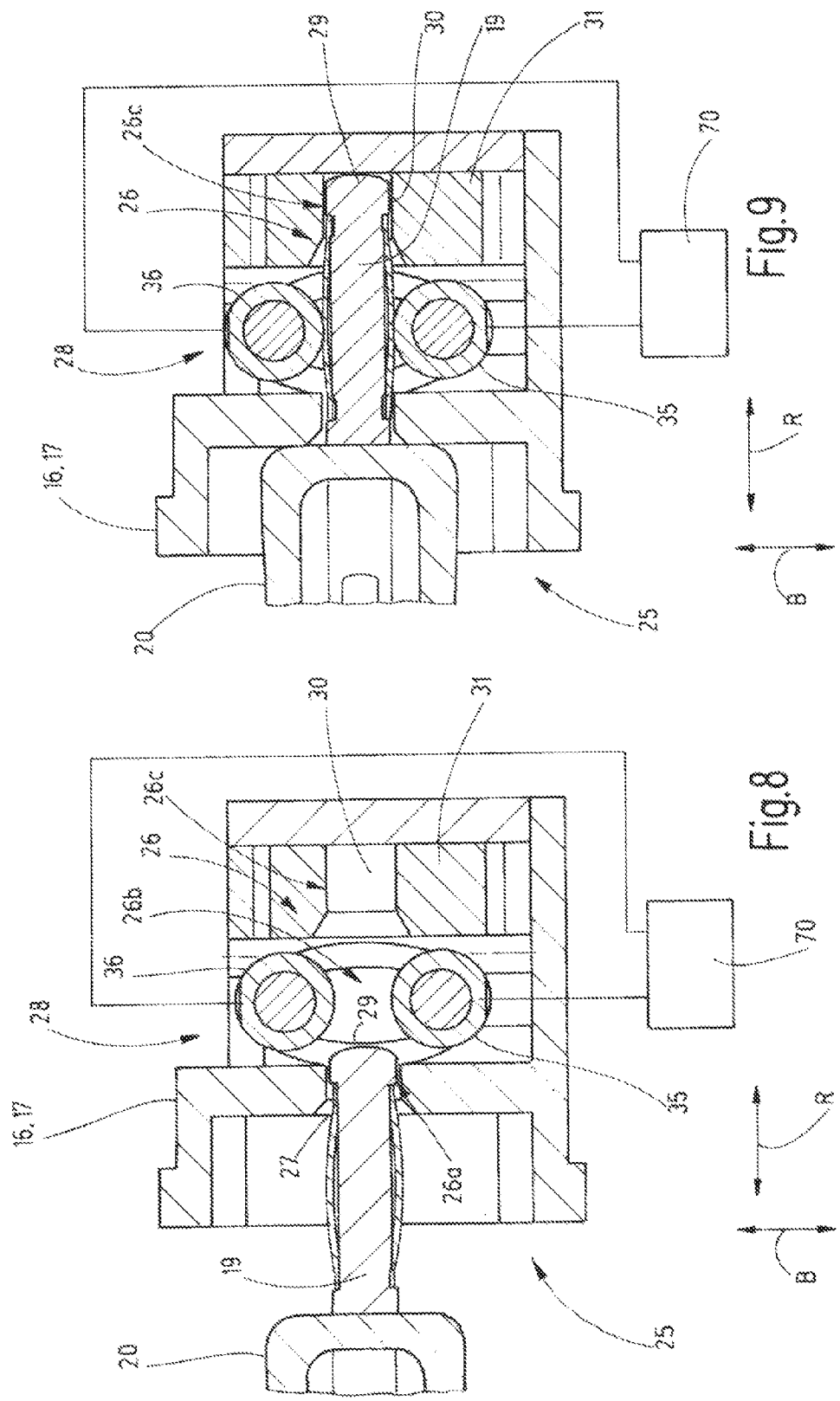

SOCKET ARRANGEMENT FOR AN ELECTROMEDICAL DEVICE

CROSS REFERENCE TO RELATED APPLICATIONS

This patent application claims the benefit of European Patent Application No. EP12165760.5 filed Apr. 26, 2012, the content of which is incorporated herein by reference in its entirety.

TECHNICAL FIELD

The invention relates to a socket arrangement for an electromedical device that can be connected to an electromedical, preferably surgical, instrument. By means of a plug, the instrument can be connected to the electromedical device via a socket arrangement. The device supplies a connected instrument with a radio-frequency voltage or a radio-frequency current. The device and the instrument are used in radio-frequency (RF) surgery. In RF surgery, voltages and currents having a frequency in the range of 200 or 300 kHz to approximately 4 MHz are used.

BACKGROUND

In conjunction with this, there is the problem that the plugs of electromedical instruments are not standardized and that there exist different plugs with several plug contact pins, said pins having different diameters and being at different distances from one another. The result of this is that not every plug of a surgical instrument can be readily connected to the associate socket arrangement of every electromedical device.

In addition, there are surgical instruments that are designed for monopolar or bipolar applications. They may comprise different plugs with different numbers of plug contact pins.

In the operating room, a fast and smooth process is important. This requires that a good mechanical and electrical connection can be established between the plug of an electromedical instrument and the socket arrangement of the device.

Publication DE 10 2007 061 483 A1 describes a surgical device connector system comprising a plurality of plug connector sockets for plugs of electromedical devices. Via a switching matrix, the plug connector sockets of the socket arrangement can be electrically connected to specific input or output sockets of the electromedical devices. This electrical connection via the switching matrix can be accomplished, for example, with data received by a data interface of the socket arrangement. The data can be transferred to the data interface by the plug of the electromedical instrument. As it were, the socket arrangement of the device performs an automatic plug detection and automatically establishes the necessary electrical connections via the switching matrix. Errors at the time of connection of the instrument to the device can be avoided in this manner. However, the switching matrix does not solve the problem of the existence of differently dimensioned plugs that need to be mechanically and electrically safely connected.

Publication DD 214 724 discloses an electrical plug connection using a socket arrangement. The socket arrangement comprises several bushes that project beyond a plate supporting the respective bush on the connection side in order to receive a plug contact pin. A recess is provided in the projecting part of the bush, into which recess is inserted a cylindrical contact element, for example. The cylindrical contact element is supported so as to be pivotable relative to the bush on the plate via a bent leg spring. On the rear side opposite the connection side, the leg spring projects from the plate and may form an electrical connection at that location. After having been inserted into the bush, the plug contact pin contacts the contact element and is electrically connected with the leg spring via said contact element.

SUMMARY

A socket arrangement is provided for an electromedical device, said socket arrangement allowing the safe mechanical and electrical contacting for various plug designs and plugs of different types of instruments.

In accordance with the invention, a socket arrangement is being suggested, said socket arrangement comprising at least one plug connector socket arranged in a housing part. For example, the housing part used is a section of the housing of the electromedical device or a separate socket housing of the socket arrangement, which socket housing can be inserted into the device. The at least one plug connector socket comprises an electrical first contact element as well as an electrical second contact element. The second contact element is supported so as to be movable relative with respect to the first contact element. The two contact elements are arranged on the opposite sides of a receiving region for a plug contact pin. Specifically, said contact elements are arranged transversely with respect to a plug-in direction, along which the plug contact pin can be inserted into the plug connector socket, at a distance from one another on diametrically opposite sides. Both contact elements delimit the receiving region for the plug contact pin in circumferential direction about the plug-in direction, preferably in one circumferential section, respectively. Preferably, viewed in circumferential direction, open regions exist between the two circumferential sections of the contact elements opposite the inside of the housing. These open regions allow the accommodation of plug contact pins having different diameters.

Referring to one exemplary embodiment, the receiving region is divided into at least two axially adjoining sections. A housing opening represents a first section of the receiving region. This is adjoined by a second section of the receiving region 26, in which the contact elements are arranged. Apart from the contact elements, the receiving region in this second section is preferably open toward the inside of the housing and, in particular, is not delimited by the bush-shaped parts of the plug connector socket as concerns the diameter. Preferably, a third section of the receiving region may adjoin the second section. In order to receive the free end of the plug contact pin, this third receiving section may be provided with a cylindrical recess in on bush part. The bush part may be an integral or a separate component of the housing. The diameter or the cross-section of the housing opening and, optionally, the recess in the bush part are greater than the maximum distance between the two contact elements or greater than the largest diameter of the plug contact pin that can be inserted. Mechanical clamping of the plug contact pin is not or only unessentially achieved in the first and, optionally, third sections of the receiving region but, in particular, only in the second section by the contact elements.

The pushing or pulling force required—due to the mechanical clamping effect—for moving a plug contact pin or a plug having several plug contact pins in the direction of extension of said pin preferably is at least 15 N and at most 60 N. Preferably, the contact elements are immovably arranged in plug-in direction and, in particular, can neither be moved back and forth nor pivoted nor rotated about an axis extending transversely to the plug-in direction. As a result of this, it is possible to generate a particularly great pushing or pulling force.

The length of the receiving space in plug-in direction of the plug contact pin is approximately 14 mm to 16 mm.

In addition, the socket arrangement comprises a spring arrangement. The spring arrangement pretensions the second contact element in the direction toward the first contact element. The pretensioning force is oriented in particular only in a direction radial with respect to the plug-in direction. Preferably, the spring arrangement is electrically insulated against the two contact elements. The spring arrangement has the effect that a plug contact pin inserted between the two contact elements is mechanically acted upon from opposite sides and is also electrically connected with the respective contact element. As a result of the fact that the two contact elements are supported so that they can be moved relative to each other, the plug contact pins having different diameters can be held in an electrically safe manner and be contacted in the plug connector socket. Also, in this case the contact elements themselves are designed so as to be rigid and they cannot be elastically deformed, even with the forces occurring here.

With the plug contact pin inserted, said pin short-circuits the two contacts. This electrical short circuit connection can be detected and/or analyzed. The first and the second contact elements may be configured so as to be identical. Preferably, the housing part has a housing opening for each plug connector socket, through which housing opening one plug connector pin, respectively, can be inserted. The contact elements are secured, in particular by the housing part, against any inadvertent touch and are not accessible from the outside when installed in the electromedical device.

With the plug contact pin not inserted in the plug connector socket, the two contact elements are in their home position. The minimum distance between the two contact elements in the home position is preferably at least great enough for the contact elements not to be in contact with each another and for a plug contact pin to be inserted. The minimum diameter of a plug contact pin that can be inserted into the plug connector socket is delimited by the minimum distance of the two contact elements from each other in their home position. The minimum distance is less than 3.7 mm or 3.8 mm, for example. The maximum diameter of a plug contact pin that can be inserted into the plug connector socket is prespecified by the maximum distance between the two contact elements, said maximum distance potentially being within a range of 5.0 mm to 5.5 mm, for example. The two contact elements can be moved relative to each other by at least more than 1 mm and, in particular, by at least 1.3 mm.

Consequently, radially resiliently elastic plug contact pins with spring blades and rigid plug contact pins without spring blades can be accommodated by the plug connector socket. A sufficient mechanical clamping effect is created for all plug types and diameters.

Referring to a preferred embodiment, the two contact elements of a shared plug connector socket are supported so as to be movable relative to the housing part. Alternatively, it is also possible to arrange only the second contact element so as to be movable relative to the housing part. Depending on the embodiment, the deflection between the two contact elements is effected by the movement of the second contact element or by the movement of both contact elements relative to the housing.

In particular, the two contact elements of a shared plug connector socket display different electrical potentials. This difference of potential can be achieved with an insulator or another means causing electrical potential differences. For example, the two contact elements are electrically insulated from each other or their potentials are different from each other, as long as no plug contact pin is inserted into the plug connector socket. In this configuration, an inserted plug contact can be detected very simply, e.g., by analyzing the potentials and/or the electrical connection between the two contact elements.

In one exemplary embodiment, the socket arrangement may comprise a plug detection device. This plug detection device is electrically connected to a data interface of the socket arrangement and/or to the two contact elements of the plug connector socket. Information regarding the connected instrument type or regarding information on the working status of the instrument can be transmitted to the device via the data interface. Additionally or alternatively, the electrical connection between the two contact elements can be detected or analyzed in order to determine that a plug contact pin has been inserted. Referring to a socket arrangement comprising several plug connector sockets, it is possible to detect the connected instrument type depending on the plug connector socket into which a plug contact pin has been inserted. For example, the plug detection device can distinguish between monopolar and bipolar electromedical surgical instruments. In addition, the plug detection device—when proper contact exists—can generate an enabling signal that signals the device that an RF voltage can be applied to the respective contact element(s) of a plug connector socket.

In a preferred embodiment, the first contact element is arranged on an electrically non-conductive first contact holder and/or the second contact element is arranged on an electrically non-conductive second contact holder. For example, the contact holder may be made of plastic material. For example, the contact element has the shape of a ring or sleeve and is movably or immovably arranged on the associate contact holder. The contact elements may also have a contour resembling a parallelepiped having a contact surface region facing the receiving region and extending in a curved manner in circumferential direction around the plug-in direction. The contact elements may consist of brass, copper, beryllium copper or another electrically conductive material, in particular a metal or metal alloy. The contact elements can be modified, in particular they may be nickel-plated and/or gold-plated. An electrically insulated support of the respective contact element can be easily accomplished via the electrical contact holder. The size and number of electrically conductive components can be minimized. Consequently, it is possible to reduce the risk that electrically conductive components act like an antenna during operation and emit undesirable electromagnetic radiation.

The movability of the two contact elements relative to one another can be very simply achieved in that the first contact holder and/or the second contact holder are movably supported on the housing part. The relative movability can be restricted in one movement direction by a guide arrangement so that a linear movement, for example, is prespecified as the relative movement. Preferably, the movement direction is oriented so as to be radial with respect to the plug-in direction. Referring to one exemplary embodiment, the two contact holders together form a guide arrangement so that they are supported in order to be movable directly next to each other in movement direction. In this embodiment, the contact holders may form an assembly unit with the contact elements and, optionally additionally, with the spring arrangement, which assembly unit can be pre-assembled and inserted as a module in the socket arrangement.

It is also possible for the second contact holder and/or the first contact holder to form a guide arrangement together with the housing part. For example, the first contact holder may be rigidly mounted to the housing part, whereas the second contact holder is then movably supported via a guide arrangement on the housing part. Referring to this embodiment, the number of movably supported parts may be reduced.

Referring to a preferred exemplary embodiment, the spring arrangement acts on at least one of the contact holders. A direct mechanical and/or electrical connection between the spring arrangement and a contact element can be prevented in this manner. The insulating contact holder is disposed to electrically separate the spring arrangement from the contact element that is respectively arranged on the contact holder.

It is possible for the spring arrangement to abut against the first contact holder and/or against the second contact holder. In doing so, the spring arrangement may be loaded on tension. Furthermore, it is possible for the spring arrangement to abut, on the one hand, directly against the first contact element or against the housing part and, on the other hand, against the second contact holder. In this modification, the spring arrangement may preferably be loaded on pressure.

In each embodiment the spring arrangement is at least a spring element that may be, for example, a leaf spring, a helical spring, an elastically deformable spring element, for example an elastomer ring. The spring arrangement may comprise several of said spring elements of the same type or of different types. The at least one spring element of a spring arrangement is preferably electrically non-conductive.

If the socket arrangement comprises at least two plug connector sockets, the two first contact elements and the two second contact elements may each also be located on a shared contact holder. As a result of this, the number of components can be reduced. Furthermore, it is possible for the two plug connector sockets to comprise a shared spring arrangement. The first and second contact elements that are arranged on a shared contact holder may be electrically insulated relative to each another.

In order to facilitate the insertion of different plugs displaying various contact pin distances, at least one plug connector socket may be configured as a double socket. It comprises two receiving regions for a plug contact pin, said receiving regions being located next to each other. The double socket may have a shared housing opening in the housing part. Both receiving regions are preferably associated with a shared first and/or a shared second contact element that comes into mechanical and electrical contact with a plug contact pin, irrespective whether or not this is plugged into one or the other receiving region of the double socket. Alternatively, it is also possible two provide two first and second contact elements that, preferably, are mechanically and/or electrically connected with each other. The flexibility of the socket arrangement is further increased by such a double socket, and the number of electromedical instruments that can be connected is increased.

The contact holders for the at least one first contact element and/or the contact holder for the at least one second contact element may extend transversely to the plug-in direction and, in one embodiment, parallel to each other.

The first contact element and/or the second contact element of a plug connector socket may be concavely curved in a direction transverse to the plug-in direction in circumferential direction around the plug-in direction. As a result of this, an improved guidance of the plug contact pin is achieved during insertion. In addition, the contact surface between the contact element and the plug contact pin can be enlarged due to the curvature. Preferably, at least a linear, and in particular a planar, abutment exists between each contact element and an inserted plug contact pin.

The first and/or the second contact elements can be rotated about an axis extending in a direction transverse to the plug-in direction and, preferably, transverse to the movement direction, for example, on the associate contact holder. The support may be accomplished via a sliding bearing or a roller bearing, for example, a ball bearing.

Additional advantageous embodiments of the invention can be inferred from the dependent patent claims as well as from the description. The description is restricted to essential features of the invention and to advantageous exemplary embodiments. Hereinafter, the invention will be explained in greater detail with reference to exemplary embodiments. The drawings are to be used for supplementary reference.

BRIEF DESCRIPTION ON THE DRAWINGS

Figure 2:
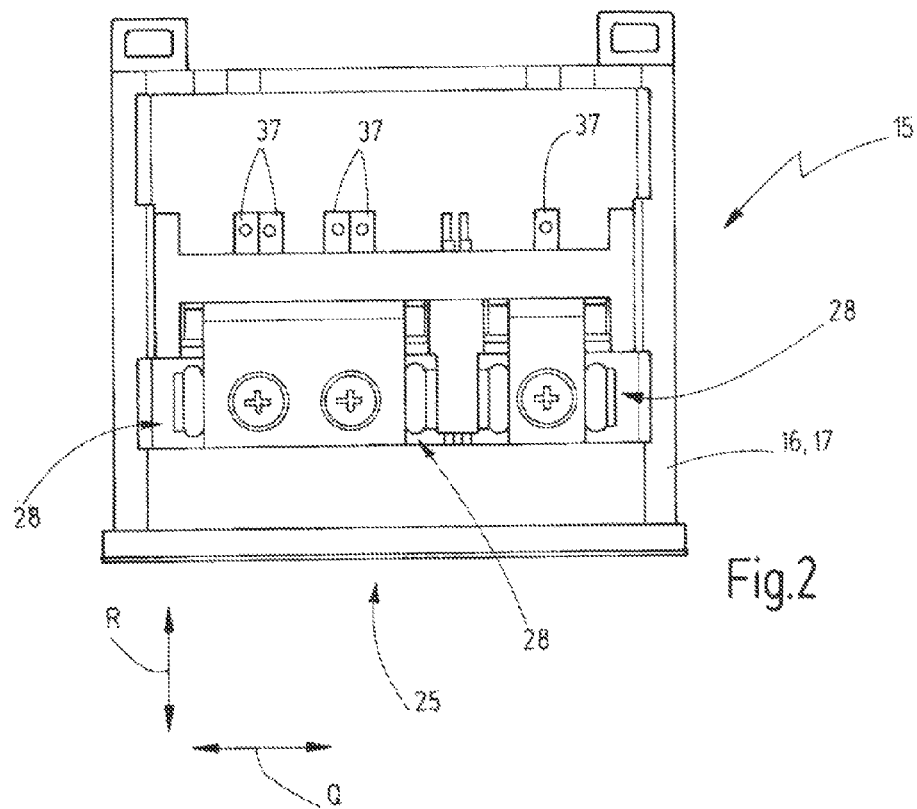

FIG. 1 a perspective illustration of a socket arrangement of an electromedical device, with a view of the connecting side of the socket housing;

FIG. 2 the socket arrangement according to FIG. 1, with a view looking down on the socket housing;

FIGS. 3 and 4 one exemplary embodiment each of a plug of an electromedical surgical instrument;

FIG. 5 a perspective illustration of a first exemplary embodiment of contact arrangements of a socket arrangement;

FIG. 6 a perspective illustration of another, second, exemplary embodiment of contact arrangements of a socket arrangement;

FIG. 7 a perspective illustration of a third exemplary embodiment of contact arrangements of a socket arrangement; and FIGS. 8 and 9 a schematic sectional view each of a plug connector socket of a socket arrangement, without and with a plug contact pin inserted.

DETAILED DESCRIPTION

FIGS. 1 and 2 show a socket arrangement 15 for an electromedical device. The socket arrangement 15 comprises several plug connector sockets 18 arranged in a housing part 16, for example a socket housing 17. The housing part consists of an electrically insulating material, in particular plastic material. Each plug connector socket 18 is disposed for the mechanical and electrical contact with a plug contact pin 19 of a plug 20 (FIGS. 3 and 4). The plug 20 belongs to an electromedical and, preferably, surgical instrument. The plug 20 for a monopolar surgical instrument has three plug contact pins 19 (FIG. 3), whereas the plug 20 for a bipolar instrument has two plug contact pins 19 (FIG. 4). The length, the thickness, as well as the exact distances of the plug contact pins 19 of a plug 20 from each other are not exactly prespecified, as a result of which deviations resulting from different manufacturers do occur. The socket arrangement 15 is configured in such a manner that plugs 20 of different types being differently dimensioned from each other and having different distances between plug contact pins 19 can be mechanically and electrically connected.

In addition to the plug connector sockets 18, the socket arrangement 15 may also comprise a data interface 23. A plug contact 24 matching the data interface 23 may also be provided on the plug 20. The instrument can transmit information to the electromedical device via the plug 20 and the plug contact 24, for example the presently existing operating mode of the instrument, the error status, information regarding the type of instrument, etc. In the exemplary embodiment as in FIG. 1, the data interface 23 is configured as a 4-pin contact.

Other forms of data interfaces 23 such as USB or mini-USB interfaces or micro-SD interfaces (FIG. 5) can also be used. Preferably, the data interface 23 has at least four pins. The connections or contacts of the data interface 23 are arranged on the connection side 25 of the socket housing 17 and the housing part 16, respectively, behind a plane that is defined by the connection side 25 of the housing part 16. Consequently, the insertion of a plug 20 that does not comprise a connection option for the data interface 23 is not impaired.

Each plug connector socket 18 has a receiving region 26 for the associate plug contact pin 19. The receiving region 26 is shown in full, in particular in FIGS. 8 and 9. The receiving region 26 extends from the connection side 25 in a plug-in direction R, in which the plug contact pin 19 is plugged into the plug connector socket 18. The receiving region 26 comprises a housing opening 27 where the housing part 16 and the socket housing 17, respectively, are open toward the connection side 25. The housing opening 27 represents a first section 26a of the receiving region 26. Adjoining the housing opening 27 is a second section 26b of the receiving region 26. The second section 26b is in the region of a contact arrangement 28 that is disposed for mechanically clamping in place and electrically contacting a plugged-in plug contact pin 19. A third section 26c of the receiving region 26 in accordance with the example is disposed to accommodate the free end 29 of the plug contact pin 19. The third section 26c is provided by a recess 30 of a socket part 31 extending in plug-in direction R. The socket part may be an integral or a separate component of the housing part 16 and thus the socket housing 17.

Over the first section 26a in the housing opening 27 and the third section 26c in the socket part 31, there is arranged a plugged-in plug contact pin 19 oriented in approximately the plug-in direction R. The cross-section or the diameter of the housing opening 27 and the recess 30 in the socket part 31 are selected in such a manner that all insertable cross-sectional forms and diameter sizes of the plug contact pins 19 can be received. In modification of the exemplary illustrations according to FIGS. 8 and 9, the outside diameter of the plug contact pin 19 thus need not necessarily correspond to the inside diameter of the housing opening 27 or the recess 30, but may also be smaller. In other words: If the cross-section or the diameter of the housing opening 27 and of the recess 30 are greater than the cross-section or the diameter of the plug contact pin, there is no considerable holding force acting on the plug contact pin—neither in the first section 26a nor in the third section 26c of the receiving region 26. The plug contact pin inserted in the plug connector socket is clamped in place, for example, only in the second section 26b by the contact arrangement 28.

FIGS. 5 through 7 show various exemplary embodiments of the contact arrangement 28. To better illustrate the contact arrangement 28, the connection side of the housing part 16 with the housing opening 27 has been left off. FIG. 7 only shows the contact arrangement without other parts of the socket arrangement 15.

Each contact arrangement 28 of a plug connector socket 18 comprises an electrically conductive first contact element 35 and an electrically conductive second contact element 36. Preferably, only two contact elements 35, 36 are provided. With the plug contact pin 19 not plugged in, the two contact elements 35, 36 are separated from each other. In the exemplary embodiment, one of the two contact elements 35, 36 and, preferably, the first contact element 35 of a shared plug connector socket 18, is connected—e. g., via a terminal lug 37 (FIG. 2)—to a corresponding input or output of the electromedical device. The other contact element 35, 36 also has a terminal lug 37 that is used for the detection of a plug contact pin 19. At least one contact element 35, 36 of the socket arrangement 15 is intended and designed to transmit a radio-frequency voltage or a radio-frequency current.

The two contact elements 35, 36 are arranged at a distance from each other on opposite sides of the receiving region 26 and, in accordance with the example, the second section 26b of the receiving region 26. Said contact elements are arranged at a minimum distance from each other in a movement direction B, radially with respect to the plug-in direction R. Preferably, the minimum distance is less than 3.7 mm. The second contact element 36 can be moved in the movement direction B relative with respect to the first contact element 35. In the first exemplary embodiment of the contact arrangement 28 as in FIG. 5, both contact elements 35, 36 of a plug connector socket 18 are supported on the housing part 16 and, the socket housing 17, respectively, so that said contact elements can be shifted in linear direction in the movement direction B. In modification of this, it is also possible for only the second contact element 36 to be supported so as to be movable relative to the housing part 16. The maximum distance of the two contact elements 35, 36 achieved by the relative movement of the two contact elements 35, 36 is 5.0 mm, for example. Consequently, plug contact pins having different diameters in the range of 3.7 mm to 5.0 mm can be plugged in between the two contact elements 35, 36.

A spring arrangement 38 is disposed to generate a pretensioning force between the two contact elements 35, 36 in movement direction B. To accomplish this, the spring arrangement 38 may apply a pulling force and/or a pressure force. In the preferred exemplary embodiment, the spring arrangement 38 comprises several separate spring elements 39. A spring element 39 may be a helical spring, a leaf spring or an elastically deformable spring element. In the exemplary embodiment according to FIG. 5, each spring arrangement comprises two elastomer rings 40, each representing a spring element 39.

In the first exemplary embodiment according to FIG. 5, the first contact element 35 is seated on a first contact holder 44 and the second contact element 36 is seated on a second contact holder 45. The contact holders 44, 45 consist of electrically non-conductive plastic material. The two contact holders 44, 45 are rod-shaped and extend in a transverse direction Q. The transverse direction Q extends at a right angle with respect to the plug-in direction R and at a right angle with respect to the movement direction B. Viewed in transverse direction Q, the elastomer rings 40 of the spring arrangement 38 are arranged on both sides of the first contact element 35, as well as of the second contact element 36. The elastomer rings 40 circumscribe the two contact holders 44, 45. Therefore, they act on both contact holders 44, 45, pulling them toward each other in movement direction B by applying the pretensioning force.

In the first exemplary embodiment of the contact arrangement 28, each of the contact holders 44, 45 is supported so as to be movable back and forth via a guide arrangement 46 in movement direction B guided on the housing part 16 and the socket housing 17, respectively. To accomplish this, the guide arrangement 46 has a slit 47 extending in movement direction B. Instead of a slit 47, it is also possible to provide a groove-like recess in the housing part 16. The associate contact holder 44, 45 comes into engagement in the slit 47. The contact holder is supported so as to be movable back and forth in movement direction B. In order to prevent a twisting of the respective contact holder 44, 45, said contact holder may have—different from its otherwise preferably cylindrical form—two flat areas that abut in a sliding manner against the slit walls of the slit 47.

As in the example, the end sections of each of the contact holders 44, 45 are supported in a slit 47 of the housing part 16. The distance of the two contact elements 35, 36 from each other in their home position can be prespecified, with the plug contact pin 19 not inserted, via the distance A measured in movement direction B between the slits 47 for the first contact holder 44 and slits 47 for the second contact holder of a contact arrangement 28.

In the first exemplary embodiment of the contact arrangement 28 according to FIG. 5, the first contact element 35 and the second contact element 36 are immovably arranged on the respectively associate contact holder 44, 45. In modification thereof, one contact element or both contact elements 35, 36 may be supported on the contact holders 44 and 45, respectively, so as to be rotatable about an axis of rotation extending in transverse direction Q. The rotary support can be accomplished with the aid of a sliding or roller bearing. As a result of this, the friction between the contact elements and the plug contact pin can be reduced during the movement of said contact pin in plug-in direction R into the receiving region 26 or out of the receiving region 26.

Each of the contact elements 35, 36 has a contact surface region 41 adjoining the receiving region 26. As is shown in FIG. 5, the contact surface region 41 of the contact elements 35, 36 may be configured so as to be curved concavely in transverse direction Q. As a result of this curvature in transverse direction Q, it is possible to achieve a certain guiding or centering of the plug contact pin 19. In modification of the embodiment shown in FIG. 5, it is also possible to provide only one of the two contact elements 35, 36 with a corresponding curvature of the contact surface region 41, whereas the respectively other contact element has an outside surface extending in a straight manner in transverse direction Q. Due to the sleeve shape, or the shape resembling a hollow cylinder, of the contact elements 35, 36 in the first exemplary embodiment of the contact arrangement 28, the contact surface regions 41 are convexly curved in plug-in direction. Additionally or alternatively, it is also possible to provide contact elements 35, 36 with contact surface regions 41 that are straight in plug-in direction, this being illustrated by the embodiments according to FIGS. 6 and 7.

The contact elements 35, 36 may have a cylindrical passage opening that can be used for the placement of the contact holders 44 and 45, respectively. The contact elements 35, 36 consist of electrically conductive material, for example, metal or a metal alloy that may also be modified, for example, gold-plated or nickel-plated. The contact elements 35, 36 may be detachably or non-detachably connected to the respective contact holder 44, 45. It is also possible to mold the contact holder 44, 45 to the contact elements 35 and 36, respectively, for example, by injection molding.

Referring to the embodiments herein, the socket arrangement 15 comprises three plug connector sockets 18, wherein one or several plug connector sockets 18 are configured as double sockets 50 comprising respectively two receiving regions 26 for one plug contact pin 19. For example, a single plug connector socket 18 is configured with only one receiving region 26 for one plug contact pin 19. The single socket 51 is disposed to act, in particular, as a reference socket that—independently of the instrument type or the plug design—is always occupied by a plug contact pin 19 when the plug 20 is inserted. Preferably, the data interface 23 is arranged between the single socket 51 and the two double sockets 50, as in the example.

The contact arrangement 28 for a double socket 50 is essentially designed in the same way as the contact arrangement 28 for a single socket 51. Each contact arrangement 28 possesses a first contact element 35 on a first contact holder 44, a second contact element 36 on a second contact holder 45, as well as a spring arrangement 38, to create a pretensioning force between the two contact holders 44, 45 and the two contact elements 35, 36, respectively. Referring to the plug connector socket 18 configured as the double socket 50, a shared first contact element 35 and a shared second contact element 36 are provided for both receiving regions 26. The form of the contact elements 35, 36 of a double socket 50 essentially corresponds to the form of two contact elements 35, 36 of the single socket 51, said contact elements being directly adjacent to each other in transverse direction Q. The contact elements 35, 36 of the double socket 50 thus have two concavely curved contact surface regions 41 adjoining each other in transverse direction Q. Alternatively, it would also be possible to provide two separate first and second contact elements for each receiving region 26 of the double socket 50, which contact elements can be connected to each other, in particular electrically and/or mechanically.

In the first exemplary embodiment shown by FIG. 5, the two contact arrangements 28 for the two double sockets 50 comprise a shared first contact holder 44 and/or a shared second contact holder 45. The spring arrangement 38 associated with the two contact holders 44, 45 is also associated with the two double sockets 50. The two first contact elements 35 and the two second contact elements 36, respectively, belonging to different plug connector sockets 18 and double sockets 50, respectively, and being arranged on a shared contact holder 44 or 45, are electrically insulated from each other via an insulator body 60. As in the example, the insulator body 60 is configured as an annular body and may be an integral component of the respective contact holder 44 or 45.

Expressed in general terms, the contact arrangements 28 of adjacent plug connector sockets 18 may comprise shared components in all embodiments, in particular a shared first contact holder 44 and/or a shared second contact holder 45 and/or a shared spring arrangement 38.

As described in conjunction with the contact arrangement 28 of the single socket 51, the contact holders 44, 45 also form a guide arrangement 46 each with the housing part 16, wherein the axial end sections of the contact holders 44, 45 are movably supported in the slits 47 in such a manner that they can be guided. Referring to the contact arrangements 28 of the two double sockets 50, the spring arrangement 38 is made up of two spring elements 39 designed as elastomer rings 40, as has already been described hereinabove.

By providing two double sockets 50 with two receiving regions 26 for a plug contact pin 19 located next to each other in transverse direction Q for a plug contact pin 19, the different relative distances of plug contact pins 19 in the plugs 20 can be tolerated. Depending on the distance of two plug contact pins 19 from each other, a pin engages in one or the other receiving region 26 of a double socket 50. In plugs 20 of monopolar instruments, all the plug connector sockets 18 are occupied by one plug contact pin 19 each. In bipolar instruments, the plug 20 has only two plug contact pins 19, one of which being associated with the single socket 51 and the other being associated with one of the two double sockets 50.

As is also shown by FIG. 5, the recess 30 in the socket part 31 of the single socket 51 is approximately cylindrical and in the double socket it has the shape of an elongated hole extending in transverse direction Q for the two adjacent receiving regions 26.

FIG. 6 shows a modified, second exemplary embodiment of the contact arrangement 28 for a plug connector socket 18 of a socket arrangement 15. The same components of the contact arrangement 28 and the socket arrangement 15 are identified by the same reference signs. Hereinafter, only differences compared with the so far described first embodiment will be explained.

The main differences of the embodiment of the contact arrangements 28 according to FIG. 6 are the shape and the configuration of the contact holders 44, 45 and the contact elements 35, 36. Different from the so far described modification, the two contact holders 44, 45 are bow-shaped or U-shaped with two legs 55 extending in the movement direction B and at a distance from each other in a transverse direction Q and with a transverse piece 56 connecting the two legs 55 in transverse direction Q. The legs 55 and the transverse piece 56 may have the shape of a parallelepiped. Between the two legs 55, there are mounted the first contact element 35 and the second contact element 36, respectively. The contact elements 35, 36 abut—preferably in a planar manner—on three sides against the two legs 55 and the transverse piece 56. On their side facing the receiving region 26 and, in particular, the second section 26b of the receiving region, the contact surface regions 41 of the contact elements 35, 36 are concavely curved in transverse direction Q as in the first exemplary embodiment. Each of the first and the second contact elements 35, 36 that belong to the double sockets 50 comprises two adjacent concavely curved contact surface regions 41. In the second exemplary embodiment shown by FIG. 6, the contact surface regions 41 are straight in plug-in direction R. As a result of this, a larger contact surface with the plug contact pin 19 can be achieved.

Another difference of the second embodiment compared with the first embodiment consists in that the two contact holders 44, 45 belonging to a plug connector socket 18 are supported directly adjacent each other so that they can be moved in a guided manner back and forth in movement direction B. The guide arrangement 46 is made up of the two contact holders 44, 45. For example, the second contact holder 45 has on both legs 55, respectively, one guide recess 57 extending in movement direction B. The guide recess 57 may be a groove or a slit. A guide projection 58 extending away from the first contact holder 44 comes into engagement in this guide recess 57 in movement direction B. The lengths of the guide recess 57 and of the guide projection 58 are adapted to the deflection of the two contact holders 44, 45 during their relative movement in movement direction B. In each relative position, the guide projection 58 remains in engagement with the guide recess 57. It is understood that, alternatively, the guide recess could also be provided on the first contact holder 44 and the guide projection 58 on the second contact holder 45. The contact holders 44, 45 comprise positioning means (not illustrated) that interact with corresponding complementary positioning means (not illustrated) on the socket part 31 and on the socket housing 17, respectively. As a result of this, positioning of the contact holders 44, 45 in R-direction and Q-direction is ensured.

The guide projection 58 and the guide recess 57, respectively, are provided on a transverse extension 59 of the leg 55. In home position, the two contact holders 44, 45 and, in particular the two transverse extensions 59 of a shared contact arrangement 28, abut—with the abutment surfaces 68—against each other due to the pretensioning force of the spring arrangement 38 in movement direction B. On their sides opposite movement direction B, transverse extensions 59 of the first contact holder 44 and the second contact holder 45 are provided with rounded—preferably shaped like a circular arc—outside surface regions 61 that are circumscribed by elastomer rings 40. In home position, two directly adjacent transverse extensions of the two contact holders 44, 45 of a contact arrangement 28 form an approximately rectangular contour—viewed in transverse direction Q—said contour having end regions that are rounded.

As in the first-described exemplary embodiment, the two contact arrangements 28 of the two double sockets 50 comprise a shared first contact holder 44 and a shared second contact holder 45 that, in any event, has two legs 55 with a transverse piece 56. Between each of the two first contact elements 35 and the two second contact elements 36 there is provided an insulator 60 for the electrical insulation of the contact elements 35 and 36 arranged on a shared contact holder 44, 45. The insulator 60 has the shape of a parallelepiped, for example, and is aligned parallel to the two legs. Said insulator may be an integral component of the respective contact holder 44, 45.

In the so far described first and second exemplary embodiments of the contact arrangement 28, both contact holders 44, 45 and thus both contact elements 35, 36 of a contact arrangement 28 are support so as to be movable in movement direction B relative to the housing part 16. The third embodiment according to FIG. 7 is different therefrom. The first contact elements 35 of each contact arrangement 28, in this case, are supported so as to be immovable relative to the housing part 16 and the socket housing 17, respectively. As in the exemplary embodiment according to FIG. 6, each of the first contact elements 35 has, adjacent each receiving region 26, a contact surface section 41 that is concavely curved in transverse direction Q. The contact holder for the first contact elements 35 is a not illustrated holding section of the housing part 16 or the socket housing 17.

Only the second contact element 36 is supported so as to be movable linearly back and forth relative to the housing part 16 in movement direction B via the second contact holder 45. The second contact holder 45 has the shape of a parallelepiped and two passage openings 63 extending in movement direction B. A pin 64, for example a screw, extends through this passage opening 63, in which case the pin 64 is directly connected with the associate first contact element 35. In one embodiment, the pin may be insulated with respect to the first contact element 35 or consist of an electrically non-conductive material. Alternatively, the pin 64 may be made of conductive material and be conductively connected to the contact element 35. This requires that the pin 64 be arranged so as to be insulated with respect to the contact element 36. The spring element 39 in the form of a helical spring 65 is arranged coaxially about the pin 64. On one side, the helical spring 65 is supported on a head 66 of the pin 64 and, on the other side, on a radial projection 67 provided in the passage opening 63, said radial projection being configured as an annular step in the exemplary embodiment. The helical spring 65 is loaded on pressure and pushes the second contact holder 45 toward the first contact element 35. As in all other embodiments, the spring elements 39 are arranged in transverse direction Q on both sides of the receiving region 26 or on both receiving regions 26 of a plug connector socket 18.

The second contact holder 45 holds the second contact element 36 whose contact surface region 41 is shorter in plug-in direction R in this case than the contact surface region 41 of the associate first contact element 35. The second contact element 36 has a straight contact surface section 41 in plug-in direction R and in transverse direction Q, whereas the contact surface sections 41 of the first contact elements 35 are concavely curved in transverse direction Q.

The functional principle of the previously explained embodiments of the contact arrangements 28 and the socket arrangements 15 will be explained hereinafter with reference to FIGS. 8 and 9.

In FIG. 8 the two contact elements 35, 36 of a contact arrangement 28 are in their home position in which their distance in movement direction B adjacent the second section 26b of the receiving region 26 is smaller than the diameter or the thickness of the smallest plug contact pin 19. When the plug contact pin 19 is being inserted into the plug connector socket 18, the two contact elements are pushed apart against the pretensioning force of the spring arrangement 38 in movement direction B and abut, subject to the pretensioning force of two opposite sides, against the plug contact pin 19 (FIG. 9). As a result of this, a good electrical, as well as a good mechanical, connection between the plug connector socket 18 and the plug contact pin 19 are achieved.

The pretensioning force of the spring arrangement 38 with the plug contact pin 19 inserted is defined to mean that the force for moving a plug contact pin 19 or a plug 20 having several plug contact pin 19 is at least 15 N and at most 60 N. In doing so, the plugging force and the pulling force fluctuate as a function of the diameter or the thickness of the plug contact pin 19 of a plug 20.

As is only illustrated in the manner of a block diagram in FIGS. 8 and 9, a plug detection arrangement 70 may be present in all the embodiments of the socket arrangement 15 comprising different contact arrangements 28. Preferably, each of the plug detection arrangements 70 is separately electrically connected to the first contact element 35 and the second contact element 36 of one or more plug connector sockets 18. In the exemplary embodiment, there exists such an electrical connection with the two contact elements 35, 36 of the single socket 51 as well as at least with one of the two double sockets 50.

The two contact elements 35, 36 of a shared plug connector socket 18 are subject to different potentials and are electrically insulated from each other when the plug or plug contact pin 19 is not inserted. When the plug contact pin 19 is being inserted, a short circuit is created between the two contact elements 35, 36. It is this potential or condition change that can be detected by the plug detection arrangement 70. For example, a test voltage can be applied to both contact elements 35, 36. When the plug contact pin 19 is not plugged in, no current flows. As soon as the plug contact pin 19 contacts both contact elements 35, 36, the electric circuit is closed and a test current will flow.

Consequently, it is also possible to use the plug detection arrangement 70 for detecting the plug connector sockets 18 that have a plug contact pin 19 inserted. If three plug contact pins 19 are detected, the plug detection arrangement 70 can output a signal to the electromedical device to indicate that the connected instrument is a monopolar instrument having one electrode connector and two control connectors. If, in contrast, only two plug contact pins 19 are detected, it may be concluded that a bipolar instrument is used.

Consequently, the plug detection arrangement 70 can output a control signal to the device that indicates the connected instrument type (monopolar or bipolar). In addition, this control signal or a separate signal can be used as an enabling signal that indicates to the device that an instrument is connected and that, accordingly, an RF voltage necessary for the operation of the instrument can be applied to the electrode connections.

It is understood that the forms and contours of the various options of the contact arrangements 28 may be modified and combined with each other. For example, the contact surface regions 41 of the contact elements 35, 36 may be configured so as to be concavely curved in transverse direction Q and/or convexly curved in plug-in direction R. It is also possible for the contact surface regions 41 to be straight in transverse direction Q and/or in plug-in direction R. In this case, any number of combinations is possible.

Considering all exemplary embodiments, only the second contact element 36 and only the second contact holder 45, respectively, or, alternatively, both contact elements 35, 36 and both contact holders 44, 45, respectively, can be guided in movement direction B preferably so as to be movable back and forth in a linear manner. In modification of the described embodiments, it is also possible for pivoting movements to be performed with a component directed in movement direction B.

The invention relates to a socket arrangement 15 comprising at least one plug connector socket 18. Each plug connector socket 18 comprises a contact arrangement 28 with two electrically conductive contact elements 35, 36 and a spring arrangement 38. The two contact elements 35, 36 are supported so as to be movable relative to each other in a movement direction B at a right angle or obliquely with respect to a plug-in direction R. The spring arrangement 38 acts on one or both contact elements 35, 36 in movement direction B. Due to the pretensioning force of the spring arrangement 38, the two contact elements 35, 36 are pushed or pulled toward each another. With the plug contact pin 19 inserted in the plug connector socket 18, the two contact elements are moved toward each other in movement direction B and abut from different sides against the plug contact pin 19. As a result of this, a mechanical clamping effect and an electrical contact are provided.

LIST OF REFERENCE SIGNS

15 Socket arrangement
16 Housing part
17 Socket housing
18 Plug connector socket
19 Plug contact pin
20 Plug
23 Data interface
24 Plug contact
25 Connection side
26 Receiving region
26a First section of the receiving region
26b Second section of the receiving region
26c Third section of the receiving region
27 Housing opening
28 Contact arrangement
29 Free end of the plug contact pin
30 Cutout
31 Socket part
35 First contact element
36 Second contact element
37 Terminal lug
38 Spring arrangement
39 Spring element
40 Elastomer ring
41 Contact surface region
44 First contact holder
45 Second contact holder
46 Guide arrangement
47 Slit
50 Double socket
51 Single socket
55 Legs
56 Transverse piece
57 Guide recess
58 Guide projection
59 Transverse extension 60 Insulator
61 Outside surface area
63 Passage opening
64 Pin
65 Helical spring
66 Head
67 Radial projection
68 Abutment surface
70 Plug detection arrangement
A Distance
B Moving direction
Q Transverse direction
R Plug-in direction

The invention claimed is:

1. Socket arrangement (15) for an electromedical device for the connection of an electromedical, preferably surgical, instrument, the socket arrangement (15) comprising
at least one plug connector socket (18) arranged in a housing part (16), the plug connector socket comprising an electrical first contact element (35) and an electrical second contact element (36) are configured to move relative to the first contact element (35), wherein the contact elements (35, 36) are arranged on opposite sides of a receiving region (26) for a plug contact pin (19);
at least one spring arrangement (38) configured to apply a pretensioning force to the second contact element (36) of the plug connector socket (18), the pretensioning force being directed toward the first contact element (35);
a plug detection arrangement (70) electrically connected with the two contact elements (35, 36) of the plug connector socket (18); wherein the first contact element (35) arranged on an electrically non-conductive first contact holder (44) or the second contact element (36) arranged on an electrically non-conductive second contact holder (45); and wherein at least one of the first contact holder (44) of the first contact element (35) or the second contact holder (45) of the second contact element (36) are supported on the housing part (16) so as to be movable in a direction transverse to a plug-in direction (R) of the plug contact pin (19).

2. Socket arrangement as in claim 1, wherein both contact elements (35, 36) of the plug connector socket (18) are supported so as to be movable relative to the housing part (16).

3. Socket arrangement as in claim 1, wherein both the contact elements (35, 36) of the plug connector socket (18) are electrically insulated from each other.

4. Socket arrangement as in claim 1, wherein both the contact holders (44, 45) comprise a guide arrangement (46) and are supported so as to be movable back and forth directly adjacent each other.

5. Socket arrangement as in claim 1, wherein at least one of the first contact holder (44) of the first contact element (35) or the second contact holder (45) of the second contact element (36) form a guide arrangement (46) together with the housing part (16) for the movable support of the respective contact holder (44, 45).

6. Socket arrangement as in claim 1, wherein the spring arrangement (38) is configured to act on at least one of the contact holders (44, 45).

7. Socket arrangement as in claim 1, wherein the spring arrangement (38) is supported by at least one of the first contact holder (44) of the first contact element (36) or by the second contact holder (45) of the second contact element (36).

8. Socket arrangement as in claim 1, wherein the spring arrangement (38) is directly supported by the first contact element (35) or by the housing part (16) and by the second contact holder (45) of the second contact element (36).

9. Socket arrangement as in claim 1, further comprising at least two plug connector sockets (18) having a first and a second contact element (35, 36) wherein both first contact elements (35) and/or both second contact elements (36) are arranged on a shared contact holder (44, 45).

10. Socket arrangement as in claim 1, wherein at least one plug connector socket (18) is configured as a double socket (50) with two receiving regions (26) for the plug contact pin (19), the receiving regions being arranged next to each other in a plug-in direction (R).

11. Socket arrangement as in claim 1, wherein at least one of the first contact element (35) or the second contact element (36) are concavely curved in a direction transverse to a plug-in direction (R).

12. Socket arrangement as in claim 1, wherein at least one of the first contact element (35) or the second contact element (36) are supported so as to be rotatable about an axis extending in a direction transverse to a plug-in direction (R).

13. Socket arrangement (15) for an electromedical device for the connection of an electromedical, preferably surgical, instrument, the socket arrangement (15) comprising
at least one plug connector socket (18) arranged in a housing part (16), the plug connector socket comprising an electrical first contact element (35) and an electrical second contact element (36) are configured to move relative to the first contact element (35), wherein the contact elements (35, 36) are arranged on opposite sides of a receiving region (26) for a plug contact pin (19);
at least one spring arrangement (38) configured to apply a pretensioning force to the second contact element (36) of the plug connector socket (18), the pretensioning force being directed toward the first contact element (35);
wherein at least one of the first contact element (35) or the second contact element (36) are supported so as to be rotatable about an axis extending in a direction transverse to a plug-in direction (R).

14. Socket arrangement as in claim 13, further comprising at least one of:
the first contact element (35) arranged on an electrically non-conductive first contact holder (44) or
the second contact element (36) arranged on an electrically non-conductive second contact holder (45).

15. Socket arrangement as in claim 14, wherein at least one of the first contact holder (44) of the first contact element (35) or the second contact holder (45) of the second contact element (36) are supported on the housing part (16) so as to be movable in a direction transverse to a plug-in direction (R) of the plug contact pin (19).

16. Socket arrangement as in claim 15, wherein both the contact holders (44, 45) comprise a guide arrangement (46) and are supported so as to be movable back and forth directly adjacent each other.

17. Socket arrangement as in claim 15,
wherein at least one of the first contact holder (44) of the first contact element (35) or the second contact holder (45) of the second contact element (36) form a guide arrangement (46) together with the housing part (16) for the movable support of the respective contact holder (44, 45).

18. Socket arrangement as in claim 1,
wherein at least one plug connector socket (18) is configured as a double socket (50) with two receiving regions (26) for the plug contact pin (19), the receiving regions being arranged next to each other in a plug-in direction (R).

\* \* \* \* \*